(12) United States Patent
Spertini (10) Patent No.: US 6,780,416 B1
(45) Date of Patent: Aug. 24, 2004

(54) BEE VENOM POLYPEPTIDES AND METHODS OF USE THEREOF

(75) Inventor: Francois Spertini, Epalinges (SE)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 0 days.

(21) Appl. No.: 09/506,978

(22) Filed: Feb. 18, 2000

(51) Int. Cl.$^7$ .................. A61K 39/00; A61K 39/35; A61K 35/64

(52) U.S. Cl. ................. 424/185.1; 424/275.1; 424/539; 530/324

(58) Field of Search ............... 424/184.1, 236.1, 424/275.1, 539; 530/500, 868, 324

(56) References Cited

U.S. PATENT DOCUMENTS

| | | | |
|---|---|---|---|
| 4,473,495 A | | 9/1984 | Patterson |
| 5,124,249 A | | 6/1992 | Khan et al. |
| 5,152,980 A | | 10/1992 | Strom et al. |
| 5,723,582 A | | 3/1998 | Ishizaka |
| 5,965,709 A | * | 10/1999 | Presta et al. |
| 6,074,673 A | * | 6/2000 | Guillen |

FOREIGN PATENT DOCUMENTS

| | | |
|---|---|---|
| GB | 2 341 389 | 3/2000 |
| WO | WO 93/19178 | 9/1993 |
| WO | WO 99/18983 | 4/1999 |
| WO | WO 00/15774 | 3/2000 |

OTHER PUBLICATIONS

Ngo et al., in The Protein Folding Problem and Tertiary Structure Prediction, 1994, Merz, et al., (ed.), Birkhauser, Boston, MA, pp. 433 and 492–495.*

Fasler et al., J. Allergy and Clinical Immunology 101(4 pt 1):521–30, Apr. 1998.*

Skolnick et al., From genes to protein structure and function: novel applications of computational approaches in the genomic era, Jan 2000, Trends in Biotech. 18(1): 34–39.*

Attwood et al., The babel of bioinformatics, Oct. 2000, Science 290 (5491):471–473.*

Banks et al Chemistry and Pharmcology of Honey–bee venom in: Piek T, ed. Venoms of the Hyemoptera. London: Academic Press; 1986, pp. 329–416.*

Burks et al Eur. J Biochem 245: 334–339; 1997.*

Stanley et al Archives of Biochemistry and Biophysics 342(2): 244–253; 1997.*

Colman et al, Effects of amino acid sequence changes on antibody–antigen interaction, 1994, A structural view of immune recognition by antibodies, pp. 33–36.*

Kämmerer, et al., J. Allergy Clin Immunol, 100, No. 1, 96–103 (1997).

Kämmerer, et al., Clincal and Experimental Allergy, 27, 1016–1026 (1997).

* cited by examiner

*Primary Examiner*—Christina Chan
*Assistant Examiner*—Phuong Huynh
(74) *Attorney, Agent, or Firm*—Mintz, Levin, Cohn, Ferris, Glovsky and Popeo, P.C.; Ivor R. Elrifi (57) ABSTRACT

The present invention provides novel protein named Api m 6. Api m 6 was identified in bee venom and is found in four isoforms, each about 8 kD. The purified Api m 6 can be used to modulate immune responses, e.g., in individuals hypersensitive to bee venom.

3 Claims, 1 Drawing Sheet

Fig. 1

SEQUENCE LISTING

<160> NUMBER OF SEQ ID NOS: 5

<210> SEQ ID NO 1
<211> LENGTH: 67
<212> TYPE: PRT
<213> ORGANISM: Apis mellifera

<400> SEQUENCE: 1

Gly Gly Phe Gly Gly Leu Gly Gly Arg Gly Lys Cys Pro Ser Asn Glu
 1               5                  10                  15

Ile Phe Ser Arg Cys Asp Gly Arg Cys Gln Arg Phe Cys Pro Asn Val
            20                  25                  30

Val Pro Lys Pro Leu Cys Ile Lys Ile Cys Ala Pro Gly Cys Val Cys
        35                  40                  45

Arg Leu Gly Tyr Leu Arg Asn Lys Lys Val Cys Val Pro Arg Ser
    50                  55                  60

Lys Cys Gly
65

<210> SEQ ID NO 2
<211> LENGTH: 69
<212> TYPE: PRT
<213> ORGANISM: Apis mellifera
<220> FEATURE:
<223> OTHER INFORMATION: Where XX at position 68 and 69 is either PL or
      LP.

<400> SEQUENCE: 2

Gly Gly Phe Gly Gly Leu Gly Gly Arg Gly Lys Cys Pro Ser Asn Glu
 1               5                  10                  15

Ile Phe Ser Arg Cys Asp Gly Arg Cys Gln Arg Phe Cys Pro Asn Val
            20                  25                  30

Val Pro Lys Pro Leu Cys Ile Lys Ile Cys Ala Pro Gly Cys Val Cys
        35                  40                  45

Arg Leu Gly Tyr Leu Arg Asn Lys Lys Val Cys Val Pro Arg Ser
    50                  55                  60

Lys Cys Gly Xaa Xaa
65

<210> SEQ ID NO 3
<211> LENGTH: 71
<212> TYPE: PRT
<213> ORGANISM: Apis mellifera

<400> SEQUENCE: 3

Phe Gly Gly Phe Gly Gly Phe Gly Gly Leu Gly Gly Arg Gly Lys Cys
 1               5                  10                  15

Pro Ser Asn Glu Ile Phe Ser Arg Cys Asp Gly Arg Cys Gln Arg Phe
            20                  25                  30

Cys Pro Asn Val Val Pro Lys Pro Leu Cys Ile Lys Ile Cys Ala Pro
        35                  40                  45

Gly Cys Val Cys Arg Leu Gly Tyr Leu Arg Asn Lys Lys Val Cys
    50                  55                  60

Val Pro Arg Ser Lys Cys Gly
65                  70

<210> SEQ ID NO 4
<211> LENGTH: 73

```
<212> TYPE: PRT
<213> ORGANISM: Apis mellifera
<220> FEATURE:
<223> OTHER INFORMATION: Where XX at position 72 and 73 is either PL or
      LP.

<400> SEQUENCE: 4

Phe Gly Gly Phe Gly Gly Phe Gly Gly Leu Gly Gly Arg Gly Lys Cys
 1               5                  10                  15

Pro Ser Asn Glu Ile Phe Ser Arg Cys Asp Gly Arg Cys Gln Arg Phe
            20                  25                  30

Cys Pro Asn Val Val Pro Lys Pro Leu Cys Ile Lys Ile Cys Ala Pro
        35                  40                  45

Gly Cys Val Cys Arg Leu Gly Tyr Leu Arg Asn Lys Lys Lys Val Cys
     50                  55                  60

Val Pro Arg Ser Lys Cys Gly Xaa Xaa
 65                  70

<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence: CYSTEINE
      SPACING MOTIF
<223> OTHER INFORMATION: Where any X can be any amino acid.

<400> SEQUENCE: 5

Cys Xaa Xaa Xaa Xaa Xaa Xaa Xaa Cys Xaa Xaa Xaa Cys Xaa Xaa
 1               5                  10                  15

Xaa Cys Xaa Xaa Xaa Xaa Xaa Xaa Xaa Cys Xaa Xaa Xaa Cys Xaa
            20                  25                  30

Xaa Xaa Cys
        35
```

BEE VENOM POLYPEPTIDES AND METHODS OF USE THEREOF

FIELD OF THE INVENTION

The present invention relates to novel polypeptides derived from bee venom and methods of use thereof, including pharmaceutical compositions useful for modulating immune responses to bee pollen.

BACKGROUND OF THE INVENTION

Bee venom (BV) is a complex mixture of antigens that can include one or more toxic polypeptides. Many of these polypeptides are hypersentizing agents and can additionally have hemolytic or neurotoxic effects.

Some individuals are hypersensitive to BV polypeptides. IgE antibodies from BV hypersensitive individuals recognize several BV toxic polypeptides. BV polypeptides, often referred to as allergens, recognized by IgE in BV hypersentive individuals can include, e.g., phospholipase $A_2$ ($PLA_2$), acid phosphatase, hyaluronidase, allergen C, and other, high molecular weight (MW) proteins.

BV hypersensitive individuals can be at high risk of an adverse reaction to a bee sting. One recognized method for preventing or minimizing serious adverse reactions resulting from a bee sting is to desensitize the individual to the allergens present in BV. This protection can be induced by a process termed venom immunotherapy (VIT).

SUMMARY OF THE INVENTION

The invention is based, in part, on the discovery of a novel bee venom protein, which has been named Api m 6. Polypeptides derived from Api m 6 polypeptides can be used, e.g., in venom immunotherapy to protect susceptible individuals from the adverse effects of a bee sting.

Accordingly, in one aspect, the invention provides a substantially pure polypeptide comprising an amino acid sequence at least 70% identical, and more preferably at least 90% identical, to the amino acid sequence of an Api m 6 polypeptide, e.g., a peptide which includes the amino acid sequence of SEQ ID NO:1. In some embodiments, the polypeptide binds to a human IgE antibody.

In other embodiments, the polypeptide includes a sequence at least 70% identical to one or more of the amino acid sequences of SEQ ID NOs:2–4. Preferably, the polypeptide has an amino acid sequence corresponding to the amino acid sequence of an Apis spp. bee venom protein, e.g., an *Apis mellifera* bee venom protein. In some embodiments, the polypeptide is glycosylated.

The polypeptide may, in some embodiments, stimulate T-cell proliferation.

The invention also features an antibody that binds to an Api m 6 protein. The antibody can be a polyclonal or a monoclonal antibody.

The invention also features a composition comprising polypeptide fragments of the Api m 6 protein, wherein the polypeptide fragments are between 6–72 amino acids in length. In preferred embodiments, the polypeptide fragments are between 20–100, 30–70, or 40–60 amino acids in length. Preferably, at least one polypeptide in the composition has an amino acid sequence that overlaps by at least 3 amino acids with at least one other polypeptide in the composition, e.g., polypeptide fragments of Api m 6 that overlap by between 5 and 10 amino acids. In the most preferred embodiments, the composition comprises of a set of polypeptide fragments that map the total length of the Api m 6 protein.

The invention also features a pharmaceutical composition that includes an Api m 6 polypeptide and a pharmaceutically acceptable carrier. In some embodiments, the pharmaceutical composition includes an additional polypeptide, e.g., a second, third, fourth, or more bee venom polypeptide or polypeptides.

The additional bee venom polypeptides can include, e.g., phospholipase $A_2$, hyaluronidase, allergen C, mellitin, adolapin, minimine, acid phosphatase, protease inhibitor, and glycosylated IgE-binding proteins, or analogs or derivatives thereof.

In another aspect, the invention features a method of modulating an immune response. The method includes administering an Api m 6 polypeptide to a subject in need thereof in an amount sufficient to inhibit an immune reaction by the subject against the polypeptide. If desired, one or more additional bee venom polypeptides may also be administered to the subject. The additional bee venom polypeptides can include, e.g., phospholipase $A_2$, hyaluronidase, allergen C, mellitin, adolapin, minimine, acid phosphatase, protease inhibitor, and glycosylated IgE-binding proteins, or analogs or derivatives thereof.

In a further aspect, the invention includes a method of identifying an individual at risk for bee venom hypersensitivity. The method includes administering to the individual an Api m 6 polypeptide and measuring an immune response raised against the polypeptide. A detectable immune response indicates that the individual is at risk for bee venom hypersensitivity. In preferred embodiments, the Api m 6 polypeptide is administered intradermally. Preferably, the Api m 6 polypeptide is administered at a concentration of less than about 1 µg/ml.

Also provided is a method of purifying an Api m 6 polypeptide. The method includes providing a cell expressing the Api m 6 polypeptide. The cell is then contacted with an antibody which binds to a polypeptide that includes an amino acid sequence at least 70% identical to the amino acid sequence of SEQ ID NO:1 under conditions which allow for formation of a polypeptide-antibody complex. The antibody-polypeptide complex is then isolated, and the Api m 6 polypeptide is recovered from the complex.

Also provided by the invention is a kit that includes, in one or more containers, an Api m 6 polypeptide, overlapping polypeptide fragments of an Api m 6 polypeptide, an anti Api m 6 polypeptide antibody (e.g., a monoclonal or polyclonal antibody), or a combination of these polypeptides or antibodies.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The invention provides a novel 8 kD bee venom protein, termed Api m 6, that was identified based on its reactivity to IgE antisera from individuals who are hypersensitive to bee venom. Four isoforms of the Api m 6 polypeptide have been identified These are: Api m 6.01, which includes the amino acid sequence shown in SEQ ID NO:1 and has a predicted molecular weight of 7,190; Api m 6.02, which includes the amino acid sequence of SEQ ID NO:2 and has a predicted molecular weight of 7,400; Api m 6.03, which includes the amino acid sequence of SEQ ID NO:3 and has a predicted molecular weight of 7,598; and Api m 6.04, which has the amino acid sequence of SEQ ID NO:4 and has a molecular weight of 7,808.

Figure 1:
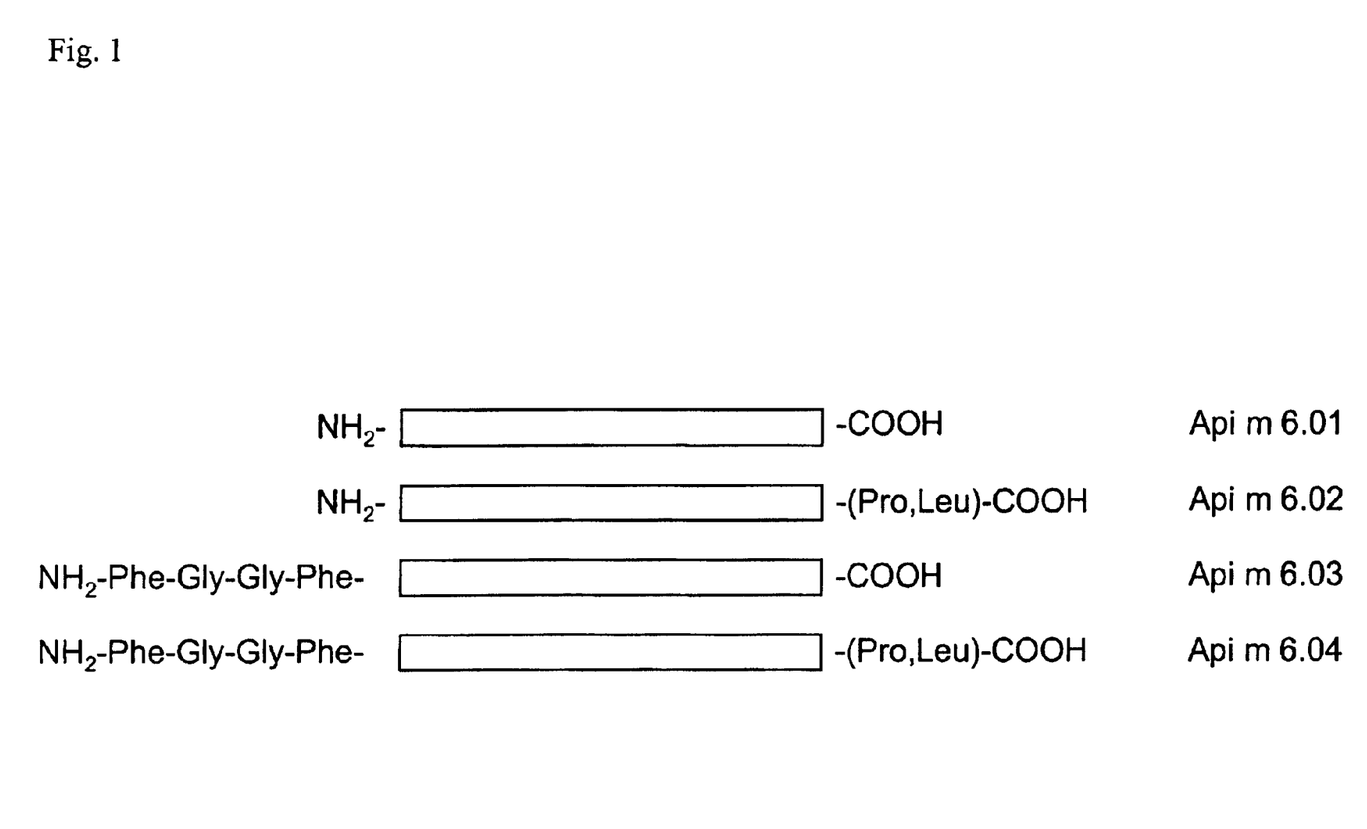
FIG. 1 is a schematic representation of the Api m 6 isoforms. The order of the amino acids in brackets was not determined. In this figure, Api m 6.01 refers to SEQ ID NO:1; Api m 6.02 refers to SEQ ID NO:2; Api m 6.03 refers to SEQ ID NO:3; Api m 6.04 refers to SEQ ID NO:4.

The four isoforms are present in approximately equimolar amounts The isoforms share a common central amino acid sequence of 67 residues and differ only in their amino and carboxyl terminus by up to 6 amino acids (FIG. 1). The common 67 amino acid core sequence is shown as Api m 6.01 (SEQ ID NO:1). Api m 6.03 (SEQ ID NO:3) and Api m 6.04 (SEQ ID NO:4) have an additional N-terminal "Phe-Gly-Gly-Phe" relative to both Api m 6.01 (SEQ ID NO: 1) and Api m 6.02 (SEQ ID NO: 2). Furthermore, Api m 6.02 and Api m 6.04 have two additional residues, Pro and Leu, at the C-terminus. The relative order of these amino acids has not yet been determined.

This novel Api m 6 protein is useful as an allergen for immunotherapy. Development of a novel bee venom immunotherapy strategy based on overlapping peptides is also described.

Sequences and Corresponding SED ID Numbers

The sequences and corresponding SEQ ID NOs discussed herein include the following:

SEQ ID NO:1 Api m 6.01 (7,190 Da) amino acid sequence (67 aa)

SEQ ID NO:2 Api m 6.02 (7,400 Da) amino acid sequence (69 aa)

SEQ ID NO:3 Api m 6.03 (7,598 Da) amino acid sequence (71 aa)

SEQ ID NO:4 Api m 6.04 (7,808 Da) amino acid sequence (73 aa)

Api m 6 Polypeptides

One aspect of the invention pertains to isolated Api m 6 polypeptides and proteins, including variants such as biologically active portions thereof. In one embodiment, native Api m 6 proteins can be isolated by an appropriate purification scheme using standard protein purification techniques. Alternatively, an Api m 6 protein or polypeptide can be synthesized chemically using standard peptide synthesis techniques, or can be produced by recombinant DNA techniques.

An "isolated" or "purified" protein or biologically active portion thereof is substantially free of material (e.g., other, contaminating proteins) from the cell suspension, tissue source, or venom preparation from which the Api m 6 protein is derived, or substantially free from chemical precursors or other chemicals when chemically synthesized. The language "substantially free of other material" includes preparations of Api m 6 protein in which the protein is separated from cellular components of the cells from which it is isolated or recombinantly produced. In one embodiment, the language "substantially free of other material" includes preparations of Api m 6 protein having less than about 30% (by dry weight) of non-Api m 6 protein (also referred to herein as a "contaminating protein"), more preferably less than about 20% of non-Api m 6 protein, still more preferably less than about 10% of non-Api m 6 protein, and most preferably less than about 5% non-Api m 6 protein. When the Api m 6 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of Api m 6 protein in which the protein is separated from chemical precursors or other chemicals which are involved in the synthesis of the protein. In one embodiment, the language "substantially free of chemical precursors or other chemicals" includes preparations of Api m 6 protein having less than about 30% (by dry weight) of chemical precursors or non-Api m 6 chemicals, more preferably less than about 20% chemical precursors or non-Api m 6 chemicals, still more preferably less than about 10% chemical precursors or non-Api m 6 chemicals, and most preferably less than about 5% chemical precursors or non-Api m 6 chemicals.

"A polypeptide having a biologically active portion of Api m 6" refers to polypeptides exhibiting activity similar, but not necessarily identical to, activity of a polypeptide of the present invention, including mature forms, as measured in a particular biological assay, with or without dose dependency. Biologically active portions of an Api m 6 protein include peptides comprising amino acid sequences sufficiently homologous to or derived from the amino acid sequence of the Api m 6 protein, e.g., the amino acid sequence shown in any of SEQ ID NOs: 1–4, which include fewer amino acids than the full length Api m 6 proteins, and exhibit at least one activity of an Api m 6 protein, e.g., the ability to stimulate T-cell proliferation or the ability to bind IgE antibody from, e.g., an individual hypersensitive to bee venom. Typically, biologically active portions comprise a domain or motif with at least one activity of the Api m 6 protein. A biologically active portion of an Api m 6 protein can be a polypeptide which is, for example, 10, 15, 25, 35, 45, 55, 60, or 65 or more amino acids in length.

In some embodiments, the Api m 6 protein has an amino acid sequence shown in any of SEQ ID NOs: 1–4. Preferably, the Api m 6 protein has the amino acid sequence of a protein isolated from bee venom from an Apis spp., e.g., *Apis mellifera*.

In other embodiments, the Api m 6 protein is substantially homologous to the sequences shown in SEQ ID NO:1–4 and retains the functional activity of the protein of SEQ ID NOs:1–4, yet differs in amino acid sequence due to natural allelic variation or mutagenesis, as described in detail below. Accordingly, in other embodiments, the Api m 6 protein is a protein which comprises an amino acid sequence at least about 45%, 55%, 65%, 75%, 85%, 90%, 95%, 97%, 98%, or even 99% homologous to any of SEQ ID NOs: 1–4, or a fragment thereof, e.g. a fragment having one or more activities of an Api m 6 protein.

When peptides derived the Api m 6 proteins or variants described herein are used to tolerize an individual sensitive to a protein allergen, e.g., by subcutaneous administration, the peptide is preferably derived from a protein allergen of the genus Apis. Long overlapping peptides comprising at least one epitope of the Apis allergen phospholipase $A_2$ have been described See, e.g., Kammerer, et al., *Clin and Exp Allergy* 27: 1016–1026 (1997) and Kammerer, et al., *J Allergy Clin Immunol* 100: 96–103 (1997).

Various Api m 6 proteins, as well as derivatives, fragments and analogs thereof, can be screened for the ability to alter and/or modulate cellular functions. This includes those relating to modulating immune response, e.g., T-cell proliferation and IgE-mediated immune reactions. The derivatives, fragments or analogs that possess the desired immunogenicity and/or antigenicity may be utilized in immunoassays, for immunization, for inhibition of the activity of an aforementioned peptide, etc. For example, derivatives, fragments or analogs that retain (or, alternatively lack or inhibit) a given property of interest may be utilized as inducers (or inhibitors) of such a property and its physiological correlates. Derivatives, fragments and analogs of an aforementioned peptide may be analyzed for the desired activity or activities by procedures known within the art.

Manipulations of the sequences included within the scope of the invention may be made at the peptide level. Included within the scope of the present invention is an aforementioned peptide (or a fragment, derivative, or analog thereof) that is differentially modified during or after translation or synthesis (e.g., by glycosylation, acetylation, phosphorylation, amidation, derivatization by known protecting/blocking groups, proteolytic cleavage, linkage to an antibody molecule or other cellular ligand, and the like). Any of the numerous chemical modification methods known within the art may be utilized including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc. In a specific embodiment, sequences of an aforementioned peptide are modified to include a fluorescent label. In another specific embodiment, an aforementioned peptide is modified by the incorporation of a heterofunctional reagent, wherein such heterofunctional reagent may be used to cross-link the members of a complex.

Complexes of analogs and derivatives of the Api m 6 proteins and variants can be chemically synthesized. For example, a peptide corresponding to a portion of an aforementioned peptide that comprises a desired domain or that mediates a desired activity in vitro, may be synthesized by use of a peptide synthesizer. In cases where natural products are suspected of being mutant or are isolated from new species, the amino acid sequence of an aforementioned protein isolated from the natural source, may be determined, e.g., by direct sequencing of the isolate protein. The peptides may also be analyzed by hydrophilicity analysis (see, e.g., Hopp and Woods, *Proc Natl Acad Sci USA* 78: 3824–3828 (1981)) which can be used to identify the hydrophobic and hydrophilic regions of the peptides, thus aiding in the design of substrates for experimental manipulation, such as in binding experiments, antibody synthesis, etc. Secondary structural analysis may also be performed to identify regions of a peptide that adopt specific structural motifs. See e.g., Chou and Fasman, *Biochem* 13: 222–223 (1974). Manipulation, translation, secondary structure prediction, hydrophilicity and hydrophobicity profiles, open reading frame prediction and plotting, and determination of sequence homologies, can be accomplished using computer software programs available in the art. Other methods of structural analysis including, but not limited to, X-ray crystallography (see, e.g., Engstrom, *Biochem Exp Biol* 11: 7–13 (1974)); mass spectroscopy and gas chromatography (see, e.g., Methods in *Protein Science*, 1997. J. Wiley and Sons, New York, N.Y.) and computer modeling (see, e.g., Fletterick and Zoller, eds., 1986. Computer Graphics and Molecular Modeling, In: *Current Communications in Molecular Biology*, Cold Spring Harbor Laboratory Press, Cold Spring Harbor, N.Y.) may also be used.

In some embodiments, one or more Api m 6 peptides are present in a composition in which one Api m 6 peptide overlaps by at least 3 amino acids with at least one other Api m 6 polypeptide in the composition. In most preferred embodiments, the peptides overlap between 5 and 10 amino acids. In certain embodiments, a composition used for tolerization includes a set of polypeptide fragments that map the entire length of the Api m 6 protein. In an additional embodiment, the amino acid sequences of one or more peptides can be produced and joined by a linker to increase sensitivity to processing by antigen-presenting cells. Such linker can be any non-epitope amino acid sequence or other appropriate linking or joining agent.

Api m 6 proteins having altered amino acid sequences can be constructed, e.g., by chemical synthesis techniques. In some embodiments, the changes do not alter the functions of the variant proteins relative to the starting Api m 6 protein, e.g., an Api m 6 protein having the amino acid sequence of any of SEQ ID NOs: 1–4. Amino acid substitutions are preferably at "non-essential" amino acid residues. A "non-essential" amino acid residue is a residue that can be altered from the wild-type sequence of Api m 6 (e.g, the sequence of any of SEQ ID NOs:1–4) without altering the biological activity, whereas an "essential" amino acid residue is required for biological activity. For example, amino acid residues that are conserved among the Api M 6 proteins from different species, e.g., different Apis spp., are predicted to be particularly unamenable to alteration The invention also includes variant Api m 6 proteins that contain changes in amino acid residues that are not essential for activity. Such Api m 6 proteins differ in amino acid sequence from any or all of SEQ ID NOs:1–4, yet retain biological activity. The variant Api m 6 proteins include in which one or more amino acid substitutions, additions or deletions are introduced into the protein.

Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in Api m 6 is preferably replaced with another amino acid residue from the same side chain family. Alternatively, in another embodiment, mutations can be introduced randomly along all or part of an Api m 6 coding sequence, to identify mutants that retain activity.

In some embodiments, a mutant Api m 6 protein can be assayed for (1) the ability to form protein:protein interactions with Api m 6 proteins, other proteins, or biologically active portions thereof, (2) complex formation between a mutant Api m 6 protein and an Api m 6 ligand; (3) the ability to stimulate T-cell proliferation; or (4) the ability to bind IgE antibodies from, e.g., the sera of an individual hypersensitive to bee venom.

A peptide derived from a protein allergen can be tested to determine whether the peptide binds IgE specific for the allergen and result in the release of mediators (i.e. histamine) from mast-cells or basophils.

T-cell stimulating activity can be tested by culturing T-cells obtained from an individual sensitive to the Api m 6 proteins and variants described herein (i.e., an individual who has an immune response to the protein allergen or protein antigen) with an Api m 6 protein or variant and determining the presence or absence of proliferation by the T-cells in response to the peptide as measured by, for example, uptake of tritiated thymidine. Stimulation indicies for responses by T-cells to peptides useful in methods of the invention can be calculated as the maximum counts per minute (CPM) taken up in response to the peptide divided by the CPM of the control medium. For example, a peptide derived from a protein allergen may have a stimulation index of about 2.0. A stimulation index of at least 2.0 is generally considered positive for purposes of defining peptides useful as immunotherapeutic agents. Preferred peptides have a stimulation index of at least 2.5, more preferably at least 3.5 and most preferably at least 5.0.

Also included in the invention are fragments of a protein having a portion of the amino acid sequence of any of SEQ ID NOs:1–4. The fragment preferably has one or more of the herein described activities of an Api m 6 protein. The fragment can be, e.g., 6–72, 30–70, or 40–60 amino acids in length.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., percent homology equals the number of identical positions divided by the total number of positions times 100).

The Api m 6 proteins, fragments, and other variants described herein can be modified. Thus, the invention includes, e.g., myristylated, glycosylated, and phosphorylated Api m 6 proteins and their derivatives.

The invention also provides Api m 6 chimeric or fusion proteins. As used herein, an Api m 6 "chimeric protein" or "fusion protein" comprises, an Api m 6 polypeptide operatively linked to a non-Api m 6 polypeptide. A "Api m 6 polypeptide" refers to a polypeptide having an amino acid sequence corresponding to Api m 6, whereas a "non-Api m 6 polypeptide" refers to a polypeptide having an amino acid sequence corresponding to a protein which is not substantially homologous to the Api m 6 protein, e.g., a protein which is different from the Api m 6 protein and which is derived from the same or a different organism. Within an Api m 6 fusion protein the Api m 6 polypeptide can correspond to all or a portion of an Api m 6 protein. In a preferred embodiment, an Api m 6 fusion protein comprises at least one biologically active portion of an Api m 6 protein. In another preferred embodiment, an Api m 6 fusion protein comprises at least two biologically active portions of an Api m 6 protein. Within the fusion protein, the term "operatively linked" is intended to indicate that the Api m 6 polypeptide and the non-Api m 6 polypeptide are fused in-frame to each other. The non-Api m 6 polypeptide can be fused to the N-terminus or C-terminus of the Api m 6 polypeptide.

For example, in one embodiment an Api m 6 fusion protein comprises an Api m 6 T-cell proliferation-inducing domain operatively linked to the extracellular domain of a second protein known to be involved in cytokine activity. Such fusion proteins can be further utilized in screening assays for compounds which modulate Api m 6 activity.

The present invention also pertains to variants of the Api m 6 proteins which function as either Api m 6 agonists (mimetics) or as Api m 6 antagonists. Variants of the Api m 6 protein can be generated by chemically synthesizing polypeptides having amino acid sequences corresponding to the agonists or antagonists. Alternatively, the mutants can be constructed by mutagenesis, e.g., discrete point mutation or truncation of the Api m 6 protein. An agonist of the Api m 6 protein can retain substantially the same, or a subset, of the biological activities of the naturally occurring form of the Api m 6 protein. An antagonist of the Api m 6 protein can inhibit one or more of the activities of the naturally occurring form of the Api m 6 protein by, for example, competitively binding to a downstream or upstream member of a cellular signaling cascade which includes the Api m 6 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the Api m 6 proteins.

For example, variants of the Api m 6 protein which function as either Api m 6 agonists (mimetics) or as Api m 6 antagonists can be identified by screening combinatorial libraries of mutants, e.g., truncation mutants, of the Api m 6 protein for Api m 6 protein agonist or antagonist activity.

Antibodies to Api m 6 Proteins

An isolated Api m 6 protein, or a portion or fragment thereof, can be used as an immunogen to generate antibodies that bind Api m 6 using standard techniques for polyclonal and monoclonal antibody preparation. A full-length Api m 6 protein can be used or, alternatively, the invention provides antigenic peptide fragments of Api m 6 for use as immunogens. The antigenic peptide of Api m 6 comprises at least 8 amino acid residues of the amino acid sequence shown in any of SEQ ID NOs:1–4 and encompasses an epitope of Api m 6 such that an antibody raised against the peptide forms a specific immune complex with Api m 6. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of Api m 6 that are located on the surface of the protein, e.g., hydrophilic regions.

An Api m 6 immunogen can prepare antibodies as explained below in the Examples. Alternatively, an Api m 6 immunogen is used to prepare antibodies by immunizing a suitable subject (e.g., rabbit, goat, mouse or other mammal) with the immunogen. An appropriate immunogenic preparation can contain, for example, a chemically synthesized Api m 6 polypeptide. The preparation can further include an adjuvant, such as Freund's complete or incomplete adjuvant, or similar immunostimulatory agent. Immunization of a suitable subject with an immunogenic Api m 6 preparation induces a polyclonal anti-Api m 6 antibody response.

Accordingly, another aspect of the invention pertains to anti-Api m 6 antibodies. The term "antibody" as used herein refers to immunoglobulin molecules and immunologically active portions of immunoglobulin molecules, i.e., molecules that contain an antigen binding site which specifically binds (immunoreacts with) an antigen, such as Api m 6. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Api m 6. The term "monoclonal antibody" or "monoclonal antibody composition", as used herein, refers to a population of antibody molecules that contain only one species of an antigen binding site capable of immunoreacting with a particular epitope of Api m 6. A monoclonal antibody composition thus typically displays a single binding affinity for a particular Api m 6 protein with which it immunoreacts.

Polyclonal anti-Api m 6 antibodies can be prepared as described above by immunizing a suitable subject with an Api m 6 immunogen. The anti-Api m 6 antibody titer in the immunized subject can be monitored over time by standard techniques, such as with an enzyme linked immunosorbent assay (ELISA) using immobilized Api m 6. If desired, the antibody molecules directed against Api m 6 can be isolated from the mammal (e.g., from the blood) and further purified by well known techniques, such as protein. A chromatography to obtain the IgG fraction. At an appropriate time after immunization, e.g., when the anti-Api m 6 antibody titers are highest, antibody-producing cells can be obtained from the subject and used to prepare monoclonal antibodies by standard techniques, such as the hybridoma technique originally described by Kohler and Milstein, *Nature* 256:495–497 (1975). See also, Brown el al., *J. Immunol.* 127:539–46 (1981); Brown et al., *J. Biol. Chem* 255:498–83 (1980); Yeh el al., *PNAS* 76:2927–31 (1976); and Yeh et al., *Int. J. Cancer* 29:269–75(1982). See also: the human B cell hybridoma technique (Kozbor et al., *Immunol Today* 4:72 (1983)), the EBV-hybridoma technique (Cole et al., (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); Lerner, Yale *J. Biol. Med.*, 54:387–402 (1981); Gefter el al, *Somatic Cell Genet.* 3:231–36(1977)). Briefly, an immortal cell line (typically a myeloma) is fused with lymphocytes (typically splenocytes) from a mammal immunized with an Api m 6 immunogen as described above, and the culture supernatants of the resulting hybridoma cells are screened to identify a hybridoma producing a monoclonal antibody that binds Api m 6.

A protocol as described in the Examples below can be used to prepare monoclonal antibodies to the herein described Api m 6 polypeptides. An example of such an antibody is the monoclonal antibody secreted by hybridoma cell line 5E11. Generally, any of the many well known protocols used for fusing lymphocytes and immortalized cell lines can be applied for the purpose of generating an anti-Api m 6 monoclonal antibody. See, e.g., Galfre et al. *Nature* 266:550–552(1977). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of he present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Api m 6, e.g., using a standard ELISA assay.

Alternative to preparing monoclonal antibody-secreting hybridomas, a monoclonal anti-Api m 6 antibody can be identified and isolated by screening a recombinant combinatorial immunoglobin library (e.g., an antibody phage display library) with Api m 6 to thereby isolate immunoglobulin library members that bind Api m 6. Kits for generating and screening phage display libraries are commercially available (e.g., the Pharmacia Recombinant Phage Antibody System, Catalog No. 27-9400-01; and the Stratagcne SurfZAP™ Phage Display Kit., Catalog No. 240612). Additionally, examples of methods and reagents particularly arnenable for use in generating and screening antibody display library can be found in, for example, U.S. Pat. No. 5,223,409; PCT International Publication Nos. WO 92/18619; WO 91/17271; WO 92/20791; WO 92/15679; WO 93/01288; WO 92/01047; WO 92/09690; WO 90/02809; and Fuchs et al, *Bio/Technology* 9:1370–1372 (1991); Hay et al. *Hum. Antibod Hybridomas* 3:81–85 (1992); Huse et al., *Science* 246:1275–1281 (1989); Griffiths et al, *EMBO J* 12:725–734 (1993); Hawkins et al., *J. Mol Biol.* 226:889–896 (1992); Clarkson et al., *Nature* 352:624–628 (1991); Gram et al., *PNAS* 89:3576–3580 (1992); Garrad et al, *Bio/Technology* 9:1373–1377 (1991); Hoogenboom et al., *Nuc. Acid Res.* 19:4133–4137 (1991); Barbas et al., *PNAS* 88:7978–7982 (1991); and McCafferty et al., *Nature* 348:552–554 (1990).

Additionally, recombinant anti-Api m 6 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, European Patent Application 171,496; Morrison et al. European Patent Application 173,494; Neuberger et al. PCT International Publication No. WO 86/01533; Cabilly et al. U.S. Pat No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al., (1987) *PNAS* 84:214–218; Nishimura et al. (1987) *Canc. Res.* 47:999–1005; Wood et al. (1985) *Nature* 314:446–449; and Shaw et al. (1988) *J. Natl.*

Cancer Inst. 80:1553–1559); Morrison, (1985) *Science* 229:1202–1207; Oi et al. (1986) *BioTechniques* 4:214; Winter, U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-Api m 6 antibody (e.g., monoclonal antibody) can be used to isolate Api m 6 by standard techniques, such as affinity chromatography or immunoprecipitation. An anti-Api m 6 antibody can facilitate the purification of natural Api m 6 from a cell suspension or bee venom and of any recombinantly produced Api m 6 expressed in host-cells. Moreover, an anti-Api m 6 antibody can be used to detect Api m 6 protein (e.g., in a cellular lysate or cell supernatant) in order to evaluate the abundance and pattern of expression of the Api m 6 protein. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Api m 6-Based Pharmaceutical Compositions

The Api m 6 proteins (allergens), peptides, and anti-Api m 6 antibodies (also referred to herein as "active compounds") of the invention can be incorporated into pharmaceutical compositions suitable for administration. Such compositions typically comprise the protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. As used herein, the phrases 'pharmaceutical composition' and 'therapeutic composition' are interchangeable.

Pharmaceutical compositions containing the Api m 6 proteins, peptides, or variants thereof can be administered to a mammal (such as a human) sensitive to Api m 6 in a form which results in a decrease in the T-cell response of the mammal upon subsequent exposure to the protein allergen. As used herein, a decrease or modification of the T-cell response of a mammal sensitive to a protein allergen is defined as non-responsiveness or diminution in symptoms to the protein allergen in the mammal, as determined by standard clinical procedures (see e.g., Varney, et al., *British Medical Journal* 302: 265–269 (1990)), including diminution in allergen induced asthmatic conditions. As referred to herein, a diminution in symptoms to an allergen includes any reduction in the allergic response of a mammal, such as a human, to the allergen following a treatment regimen with a peptide as described herein. This diminution in symptoms may be determined subjectively in a human (e.g., the patient feels more comfortable upon exposure to the allergen), or clinically, such as with a standard skin test.

Administration of the therapeutic compositions of the present invention to desensitize or tolerize an individual to a protein allergen or other protein antigen can be carried out using procedures, at dosages and for periods of time effective to reduce sensitivity (i.e., to reduce the allergic response) of the individual to a protein allergen or other protein antigen. Effective amounts of the therapeutic compositions will vary according to factors such as the degree of sensitivity of the individual to the protein allergen, the age, sex, and weight of the individual, and the ability of the peptide(s) to elicit an antigenic response in the individual. Dosage regimes may be adjusted to provide the optimum therapeutic response. For example, several divided doses may be administered daily or the dose may be proportionally reduced as indicated by the exigencies of the therapeutic situation.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of toxicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Administration, e.g., subcutaneous administration, of an Api m 6 protein or variant peptide as described herein to a mammal, such as a human, can tolerize or anergize appropriate T-cell subpopulations such that they become unresponsive to the protein allergen and do not participate in stimulating an immune response upon subsequent exposure. In addition, administration of such a peptide may modify the lymphokine secretion profile as compared with exposure to the naturally-occurring protein allergen or portion thereof (e.g., result in a decrease of IL-4 and/or an increase in IL-2). Furthermore, exposure to the peptide may influence T-cell subpopulations which normally participate in the response to the allergen such that these T-cells are drawn away from the site(s) of normal exposure to the allergen toward the site of therapeutic administration of the peptide. This redistribution of T-cell subpopulations may ameliorate or reduce the ability of an individual's immune system to stimulate the usual immune response at the site of normal exposure to the allergen, resulting in a diminution in allergic symptoms.

In addition, administration of the above-described Api m 6 proteins, peptides or their variants may result in lower levels of IgE stimulation activity. Preferably, administration results in minimal IgE stimulating activity. As used herein, minimal IgE stimulating activity refers to IgE production that is less than the amount of IgE production and/or IL-4 production stimulated by the whole Api m 6 protein allergen.

Pharmaceutical compositions suitable for injectable use include sterile aqueous solutions (where the peptides or protein are water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fingi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an Api m 6 protein, peptides or anti-Api m 6 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transderrnal administration, penetrants appropriate to the barrier to be permeated used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

It is also possible to modify the structure of peptides useful in methods of the invention for such purposes as increasing solubility, enhancing therapeutic or preventive efficacy, or stability (e.g., shelf life ex vivo, and resistance to proteolytic degradation in vivo). A modified peptide can be produced in which the amino acid sequence has been altered, such as by amino acid substitution, deletion, or addition, to modify immunogenicity and/or reduce allergenicity, or to which a component has been added for the same purpose. For example, the amino acid residues essential to T-cell epitope function can be determined using known techniques (e.g., substitution of each residue and determination of presence or absence of T-cell reactivity). Those residues shown to be essential can be modified (e.g., replaced by another amino acid whose presence is shown to enhance T-cell reactivity), as can those which are not required for T-cell reactivity (e.g., by being replaced by another amino acid whose incorporation enhances T-cell reactivity but does not diminish binding to relevant MHC). Another example of a modification of peptides is substitution of cysteine residues preferably with alanine, or glutamic acid, or alternatively with serine or threonine to minimize dimerization via disulfide linkages.

In order to enhance stability and/or reactivity, peptides can also be modified to incorporate one or more polymorphisms in the amino acid sequence of a protein allergen resulting from natural allelic variation. Additionally, D-amino acids, non-natural amino acids or non-amino acid analogues can be substituted or added to produce a modified peptide within the scope of this invention Furthermore, peptides can be modified to produce a peptide-PEG conjugate. Modifications of peptides can also include reduction/alkylation (Tarr in: *Methods of Protein Microcharacterization*, J. E. Silver, ed Humana Press, Clifton, N.J., pp 155–194 (1986)); acylation (Tarr, supra); esterification (Tarr, supra); chemical coupling to an appropriate carrier (Mishell and Shiigi, eds., *Selected Methods in Cellular Immunology*, W H Freeman, San Francisco, Calif. (1980); U.S. Pat. No. 4,939,239); or mild formalin treatment (Marsh *International Archives of Allergy and Applied Immunology* 41:199–215 (1971)).

To facilitate purification and potentially increase solubility of peptides, it is possible to add reporter group(s) to the peptide backbone. For example, poly-histidine can be added to a peptide to purify the peptide on immobilized metal ion affinity chromatography. Hochuli, et al., *Bio/Technology*, 6:1321–1235 (1988). In addition, specific endoprotease cleavage sites can be introduced, if desired, between a reporter group and amino acid sequences of a peptide to facilitate isolation of peptides free of irrelevant sequences. In order to successfully desensitize an individual to a protein antigen, it may be necessary to increase the solubility of a peptide by adding functional groups to the peptide or by not including hydrophobic T-cell epitopes or regions containing hydrophobic epitopes in the peptide.

To potentially aid proper antigen processing of T-cell epitopes within a peptide, canonical protease sensitive sites can be recombinantly or synthetically engineered between regions, each comprising at least one T-cell epitope. For example, charged amino acid pairs, such as KK or RR, can be introduced between regions within a peptide during synthesis.

The invention further encompasses at least one therapeutic composition useful in treating a disease which involves an immune response to protein antigen (e.g., an allergen, an autoantigen, etc.) comprising at least one peptide having a sufficient percentage of the T-cell epitopes of the protein antigen such that in a substantial percentage of a population of individuals sensitive to the protein antigen, the response of such individuals to the protein antigen is substantially diminished, with the provision that the at least one peptide does not comprise the entire protein antigen.

Kits Including Api m 6 Proteins or Antibodies

The present invention additionally provides kits for diagnostic use that are comprised of one or more containers containing an Api m 6 protein or Api m 6 antibody and, optionally, a labeled binding partner to the antibody. The label incorporated into the antibody may include, but is not limited to, a chemiluminescent, enzymatic, fluorescent, colorimetric or radioactive moiety. The kit may, optionally, further comprise a predetermined amount of a purified aforementioned peptide, or nucleic acids therefor, for use as a diagnostic, standard, or control in the aforementioned assays.

EXAMPLES

The invention will be further described in the following examples, which do not limit the scope of the invention described in the claims. The following examples illustrate the identification, characterization and applications of Api m 6 protein.

Example 1

Purification of Api m 6 Isoforms

The Api m 6 protein was identified in studies examining the reactivity of IgE-sera derived from patients hypersensitive to purified bee venom (BV) proteins.

Serum and peripheral blood mononuclear cells (PBMC) were obtained from BV hypersensitive patients (grade II–IV, according to Mueller's classification). Mueller, *J Asthma Res* 3: 331–333 (1966). All patients had BV specific IgE ($\geq$0.35 kU/1; CAP® system Pharmacia, Uppsala, Sweden) and positive intradermal skin tests ($\geq$0.1 µg/ml, Pharmalgen®, ALK, Hirsholm, Denmark).

BV proteins were separated by 15% SDS-PAGE (sodium dodecyl sulfate-polyacrylamide gel electrophoresis) under non-reducing conditions and blotted to PVDF membranes in CAPS/methanol buffer (10 mM CAPS, 10% methanol, pH 11). Membranes were blocked with non-fat milk (5%) in phosphate buffered salt solution containing 0.1% Tween 20 (PBS-Tween), then incubated with patients' sera (1/10 in PBS-Tween) for 24 h at 4° C. Specific IgE binding was detected using a biotinylated monoclonal mouse anti-human IgE antibody (Pharningen, Hamburg, Germany) followed by incubation with streptavidin conjugated horseradish peroxidase (HRP) (UBI, Lucerna Chem AG, Luzem, Switzerland). Peroxidase reactivity was visualized by enhanced chemiluminescence (ECL, Amersham, UK).

Analysis of IgE sera from 43 patients reactive with separated BV proteins revealed a previously undescribed band at about 8 kD in 18 (42%) of the samples. The 8 kDa protein corresponding to the observed 8 kDa band was purified from other BV proteins by size exclusion chromatography. Chromatography was performed by lyophilizing whole BV (*Apis mellifera*) (Latoxan, Rosans, France) in 50% formic acid. Particles were removed by centrifugation and filtration prior to sample application to a BioRad P-60 column (2.5×100 cm) (BioRad, Glattbrugg, Switzerland) equilibrated in 50% formic acid. Acidic conditions were used to minimize melittin tetramer formation Bello, et al., *Biochemistry* 21: 461–465 (1982). Fractions of 4 ml were collected at a flow rate of 6.5 ml/h Each fraction was lyophilized, dissolved in 0.02 N acetic acid and analyzed by SDS-PAGE. Laemmili, *Nature* 227: 680–685 (1970). Fractions containing the 8 kDa band eluted in a broad peak between the peaks of two other bee venom proteins, $PLA_2$ and melittin. MALDI-TOF mass spectrometry analysis of these fractions revealed the presence of four proteins with molecular weights of 7,190, 7400, 7,598, and 7,808 Da.

The four proteins were further purified by reverse phase HPLC using two runs through a $C_4$ column (Phenomex W-Porex 5; 250×46 mm; Rancho Palos Verdes, Calif., USA). Water-acetonitrile gradient was used for separation (buffer A: 10% acetonitrile, 0.1% trifluoroacetic acid in water; buffer B: 90% acetonitrile, 0.1% trifluoroacetic acid in water). All four proteins were recognized by IgE from a BV hypersensitive patient that was positive for the 8 kDa protein in the initial screening. The four proteins were named Api m 6.01, Api m 6.02, and Api m 6.03, and Api m 6.04, respectively.

Example 2

Elucidation of the Amino Acid Sequence of Api m 6 Isoforms

The amino acid sequence of the 8 kDa protein isoforms was determined by two approaches: N-terminal sequence analysis by Edman degradation and C-terminal sequencing using carboxypeptidases in combination with mass spectrometry.

Amino-terminal sequence analysis of proteins and proteolytic fragments was carried out with a pulse-liquid phase microsequencer, model 477A (Applied Biosystems, Foster City, Calif.) using standard programs. Proteins were reduced (8 M Urea, 0.15 M Tris-HCl, 2.5 mM 1,4-dithiothreitol (DTT), pH 8.6) and alkylated (7.5 mM sodium iodoacetate) prior to desalting on a $C_8$ reverse phase column. Alkylated 7.6 kD (Api m 6.03) protein was incubated with trypsin (sequencing grade, Boehringer Mannheim AG, Rotkreuz, Switzerland) overnight at room temperature (RT) (50 mM Tris-H.Cl, pH 8.6); fragments were separated by HPLC ($C_8$column 5: m HAIsil™, 2.1×100 mm; Higgins Analytical Inc.).

Carboxyl terminal sequence analysis of proteins and proteolytic fragments was performed by matrix-assisted laser desorption-ionization time of flight (MALDI-TOF) mass spectrometry, on a voyager-DE™RP (PerSeptive Biosystems, Framingham, Mass., USA). Patterson, et al., *Anal Chem* 67: 3971–3978 (1995). V8 proteinase (Endoproteinase Glu-C) was purchased from Promega (Zurich, Switzerland) and used according to the manufacturer's instructions. Endoproteinase Arg-C sequencing grade, endoproteinase Asp-N sequencing grade, carboxypeptidase Y sequencing grade and carboxypeptidase A were purchased from Boehringer Mannheim AG (Rotkreuz, Switzerland). Enzymatic fragmentation with Arg-C was carried out at either room temperature (RT) or 4° C. in 15 mM HEPES buffer (pH 8) with 10 mM DTT. The enzyme to protein-ratio was 1/50 (w/w). The reaction was stopped by adding matrix solution (saturated solution of sinapinic acid, 10 mg/ml, in acetonitrile/water 30/70% (v/v)). Fragments from Asp-N digestion (enzyme to protein ratio of 1/125 (w/w) in 15 mM ammonium acetate buffer, pH 6.5) of reduced proteins (2 mM DTT in water, 37° C. over night) were separated by HPLC for further analysis. Determination of free SH-groups of cysteines was done by incubation with N-ethylmaleimide (NEM). C-terminal amino acids were determined by incubation of proteins with carboxypeptidase A (enzyme to protein ratio of 1/10 to 1/100 (w/w) in 15 mM HEPES buffer, pH 7.5) or carboxypeptidase Y (enzyme to protein ratio of 1/10 to 4/100 (w/w) in, 15 mM ammonium acetate, pH 6) at 4° C. or room temperature. Experimental conditions were optimized for each substrate preparation. The reaction was stopped by the addition of matrix solution. The first 48 amino acids were resolved by direct sequencing of the reduced and alkylated protein. Overlapping internal segments were obtained by sequencing of HPLC purified tryptic peptides. C-terminal sequence, on the other hand, could only be determined by sequencing using carboxypeptidases. C-terminal residues were resolved in independent experiments using either carboxypeptidase Y or A. Long stretches of sequence data obtained by N-terminal analysis were furthermore confirmed by C-terminal analysis. The amino acid sequences of the Api m 6 isoforms is shown in Table 1.

Api m 6.03 was further analyzed by mass spectrometry after incubation with either endoproteinase Arg-C, Asp-N or V8. Signals for proteolytic peptides were consistent with theoretical mass of expected fragments and confirmed the positions of arginine, aspartate and glutamate residues.

EMBL and SWISS PROT data base searches for protein sequence homology and computer assisted protein analysis were done applying the Wisconsin Package Version 9.1 software (Genetics Computer Group, Madison, Wis., USA). Database searches revealed that Api m 6 contained an epidermal growth factor-like domain signature which is shared by many otherwise unrelated proteins. Davis, *New Biol.* 2:410–419 (1990). No obvious homology to known proteins was found even when a profile search with the particular cysteine spacing motif "CX8CX3CX3CX8CX3CX3C" (SEQ ID NO:5), where X is any amino acid, was performed.

Example 3

Generation of Antibodies to Api m 6 Isoforms

A B cell hybridoma line producing monoclonal anti-Api m 6.03 (SEQ ID NO:3) antibodies was established from mice immunized with Api m 6.03 (SEQ ID NO:3). The hybridoma culture supernatant was diluted 1/25,000 in PBS-Tween 1% milk and incubated with membranes for 1 hour at RT. Specific antibody binding was detected with HRP conjugated sheep anti-mouse Ig antibody (Amersham, UK) and peroxidase reactivity was visualized by enhanced chemiluminescence.

Equivalents

From the foregoing detailed description of the specific embodiments of the invention, it should be apparent that a novel bee venom allergen has been described. Although particular embodiments have been disclosed herein in detail, this has been done by way of example for purposes of illustration only, and is not intended to be limiting with respect to the scope of the appended claims which follow

TABLE 1

Amino Acid Sequences of Api m 6.01, 6.02, 6.03, and 6.04

| | |
|---|---|
| $NH_2$-GGFGGLGGRGKCPSNEIFSRCDGRCQRFCPNVVPKPLCIKICAPGCVCRLGYLRNKKKVCVPRSKCG-COOH | (SEQ ID NO: 1) |
| $NH_2$-GGFGGLGGRGKCPSNEIFSRCDGRCQRFCPNVVPKPLCIKICAPGCVCRLGYLRNKKKVCVPRSKCG (P,L)-COOH | (SEQ ID NO: 2) |
| $NH_2$-FGGFGGFGGLGGRGKCPSNEIFSRCDGRCQRFCPNVVPKPLCIKICAPGCVCRLGYLRNKKKVCVPRSKCG-COOH | (SEQ ID NO: 3) |
| $NH_2$-FGGFGGFGGLGGRGKCPSNEIFSRCDGRCQRFCPNVVPKPLCIKICAPGCVCRLGYLRNKKKVCVPRSKCG (P,L)-COOH | (SEQ ID NO: 4) |

What is claimed is:

1. A method of modulating an immune response to bee venom, said method comprising administering a substantially pure bee venom polypeptide consisting of the amino acid sequence of SEQ ID NO:1 to a subject in need thereof in an amount sufficient to inhibit a T-cell immune response by the subject against said bee venom.

2. The method of claim 1, further comprising administering a second bee venom polypeptide to said subject, wherein the second bee venom polypeptide is selected from the group consisting of phospholipase $A_2$, hyaluronidase, allergen C, mellitin, adolapin, minimine, and acid phosphatase.

3. The method of claim 1, further comprising administering one or more additional bee venom polypeptides to said subject, wherein one or more additional bee venom polypeptides is selected from the group consisting of phospholipase $A_2$, hyaluronidase, allergen C, mellitin, adolapin, minimine, and acid phosphatase.

* * * * *